United States Patent [19]
Mansour et al.

[11] Patent Number: 6,069,250
[45] Date of Patent: *May 30, 2000

[54] METHOD AND COMPOSITIONS FOR THE SYNTHESIS OF DIOXOLANE NUCLEOSIDES WITH β-CONFIGURATION

[75] Inventors: Tarek Mansour; Alex Cimpoia, both of Montreal; Krzysztof Bednarski, Laval, all of Canada

[73] Assignee: Biochem Pharma Inc., Quebec, Canada

[ * ] Notice: This patent is subject to a terminal disclaimer.

[21] Appl. No.: 09/251,431

[22] Filed: Feb. 17, 1999

Related U.S. Application Data

[62] Division of application No. 08/849,722, filed as application No. PCT/CA96/00845, Dec. 13, 1996, Pat. No. 5,922,867.

[30] Foreign Application Priority Data

Dec. 14, 1995 [GB] United Kingdom ............ 9525606

[51] Int. Cl.[7] .......... C07D 473/04; C07D 473/16; C07D 473/18; C07D 473/32; C07D 473/34; C07D 473/40; C07D 239/26

[52] U.S. Cl. .......... 544/264; 544/265; 544/272; 544/280; 544/298; 544/309; 544/312; 544/317

[58] Field of Search .................... 544/264, 265, 544/272, 280, 298, 309, 312, 317

[56] References Cited

FOREIGN PATENT DOCUMENTS 0 577 304 A1  5/1993  European Pat. Off. .

92 14729  9/1992  WIPO .

OTHER PUBLICATIONS

Bodanszky et al. The Practice of Peptide Synthesis. P. 138–147, 1994.
Tetrahedron Letters, vol. 29 No. 11, 1988, pp. 1239–1242, "A New Synthesis of 2', 3'–dideoxynucleosides for AIDS Chemothereapy".
Tetrahedron Letters, vo. 33, No. 46, 1992, pp. 6949–6952, Oxidative Degradation of L–Ascorbic Acid Acetals to 2',3'–Dideoxy–3'–Oxaribofuranosides...
Journal of the America Chemical Society, vol. 113, 1991, pp. 9377–9379, In Situ Complexaton Directs the Stereochemistry of...

Primary Examiner—Mukund J. Shah
Assistant Examiner—V Balasubramanian
Attorney, Agent, or Firm—Arent, Fox, Kintner, Plotkin, Kahn

[57] ABSTRACT

The present invention relates to methods and compositions for preparing biologically important nucleoside analogues containing 1,3-dioxolane sugar rings. In particular, this invention relates to the stereoselective synthesis of the beta (cis) isomer by glycosylating the base with an intermediate of formula (II) below a temperature of about −10° C.

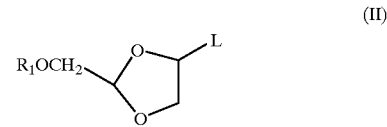

(II)

wherein $R_1$ and L are as defined herein.

14 Claims, No Drawings

METHOD AND COMPOSITIONS FOR THE SYNTHESIS OF DIOXOLANE NUCLEOSIDES WITH β-CONFIGURATION

This application is a Divisional of application Ser. No. 08/849,722, filed Jun. 26, 1997, now U.S. Pat. No. 5,922,867, which is a PCT/CA96/00845, Dec. 13, 1996.

FIELD OF THE INVENTION

The present invention relates to methods and compositions for preparing nucleoside analogues containing dioxolane sugar rings. In particular, the invention relates to the stereoselective synthesis 1,3-dioxolane nucleosides having β or cis configuration.

BACKGROUND OF THE INVENTION

Nucleosides and their analogues represent an important class of chemotherapeutic agents with antiviral, anticancer, immunomodulatory and antibiotic activities. Nucleoside analogues such as 3'-azido-3'-deoxythymidine (AZT), 2',3'-dideoxyinosine (ddI), 2',3'-dideoxycytidine (ddC), 3'-deoxy-2',3'-didehydrothymidine ($d_4T$) and (-)-2'-deoxy-3'-thiacytidine (3TC™) are clinically approved for the treatment of infections caused by the human immunodeficiency viruses. 2'-Deoxy-2'-methylidenecytidine (DMDC, Yamagami et al. *Cancer Research* 1991, 51, 2319) and 2'-deoxy-2',2'-difluorocytidine (gemcytidine, Hertel et al. *J. Org. Chem.* 1988, 53, 2406) are nucleoside analogues with antitumor activity. A number of C-8 substituted guanosines such as 7-thia-8-oxoguanosine (Smee et al. *J. Biol. Response Mod.* 1990, 9, 24) 8-bromoguanosine and 8-mercaptoguanosine (Wicker et al. *Cell Immunol.* 1987, 106, 318) stimulate the immune system and induce the production of interferon. All of the above biologically active nucleosides are single enantiomers.

Recently, several members of the 3'-heterosubstituted class of 2',3'-dideoxynucleoside analogues such as 3TC™ (Coates et al. *Antimicrob. Agents Chemother.* 1992, 36, 202), (-)-FTC (Chang et al. *J. Bio. Chem.* 1992, 267, 13938–13942) (-)-dioxolane C (Kim et al. *Tetrahedron Lett.* 1992, 33, 6899) have been reported to possess potent activity against HIV and HBV replication and possess the β-L absolute configuration. (-)-Dioxolane C has been reported to possess antitumor activity (Grove et al. *Cancer Res.* 1995, 55, 3008–3011). The dideoxynucleoside analogues (-)-dOTC and (-)-dOTFC (Mansour et al. *J. Med. Chem.* 1995, 38, 1–4) were selective in activity against HIV-1.

For a stereoselective synthesis of nucleoside analogues, it is essential that the nucleobase be introduced predominately with the desired relative stereochemistry without causing anomerization in the carbohydrate portion. One approach to achieve this is to modify the carbohydrate portion of a preassembled nucleoside by a variety of deoxygenation reactions (Chu et al. *J. Org. Chem.* 1989, 54, 2217–2225; Marcuccio et al. *Nucleosides Nucleotides* 1992, 11, 1695–1701; Starrett et al. *Nucleosides Nucleotides* 1990, 9, 885–897, Bhat et al. *Nucleosides Nucleotides* 1990, 9, 1061–1065). This approach however is limited to the synthesis of those analogues whose absolute configuration resembles that of the starting nucleoside and would not be practical if lengthy procedures are required to prepare the starting nucleoside prior to deoxygenation as would be the case for β-L dideoxynucleosides. An alternative approach to achieve stereoselectivity has been reported which requires assembling the nucleoside analogue by a reaction of a base or its synthetic precursor with the carbohydrate portion under Lewis acid coupling procedures or SN-2 like conditions.

It is well known in the art that glycosylation of bases to dideoxysugars proceed in low stereoselectivity in the absence of a 2'-substituent on the carbohydrate rings capable of neighboring group participation. Okabe et al. (*J. Org. Chem.* 1988, 53, 4780–4786) reported the highest ratio of β:α isomers of ddC of 60:40 with ethylaluminium dichloride as the Lewis acid. However, with a phenylselenenyl substituent at the C-2 position of the carbohydrate (Chu et al. *J. Org. Chem.* 1980, 55, 1418–1420; Beach et al. *J. Org. Chem.* 1992, 57, 3887–3894) or a phenylsulfenyl moiety (Wilson et al. *Tetrahedron Lett.* 1990, 31, 1815–1818) the β:α ratio increases to 99:1. To overcome problems of introducing such substituents with the desired α-stereochemistry, Kawakami et al. (*Nucleosides Nucleotides* 1992, 11, 1673–1682) reported that disubstitution at C-2 of the sugar ring as in 2,2-diphenylthio-2,3-dideoxyribose affords nucleosides in the ratio of β:α=80:20 when reacted with silylated bases in the presence of trimethylsilyltriflate (TMSOTf) as a catalyst. Although this strategy enabled the synthesis of the β2-anomer, removal of the phenylthio group proved to be problematic.

Due to the limited generality in introducing the C-2 substituent stereoselectively, synthetic methodologies based on electrophilic addition of phenyl sulfenyl halides or N-iodosucciniimides and nucleobases to furanoid glycal intermediates have been reported (Kim et al. *Tetrahedron Lett.* 1992, 33, 5733–5376; Kawakami et al. *Heterocycles* 1993, 36, 665–669; ; Wang et al. *Tetrahedron Lett.* 1993, 34, 4881–4884; El-laghdach et al. *Tetrahedron Lett.* 1993, 34, 2821–2822). In this approach, the 2'-substituent is introduced in situ however, multistep procedures are needed for removal of such substituents.

SN-2 like coupling procedures of 1-chloro and 1-bromo 2,3-dideoxysugars have been investigated (Farina et al. *Tetrahedron Lett.* 1988, 29, 1239–1242; Kawakami et al. *Heterocycles* 1990, 31, 2041–2053). However, the highest ratio of β to α nucleosides reported is 70:30 respectively.

In situ complexation of metal salts such as $SnCl_4$ or $Ti(O-Pr)_2Cl_2$ to the α-face of the sugar precursor when the sugar portion is an oxathiolanyl or dioxolanyl derivative produces β-pyrimidine nucleosides (Choi et al. *J. Am. Chem. Soc.* 1991, 113, 9377–9379). Despite the high ratio of β- to α-anomers obtained in this approach, a serious limitation with enantiomerically pure sugar precursor is reported leading to racemic nucleosides (Beach et al. *J. Org. Chem.* 1992, 57, 2217–2219; Humber et al. *Tetrahedron Lett.* 1992, 32, 4625–4628; Hoong et al. *J. Org. Chem.* 1992, 57, 5563–5565). In order to produce one enantiomeric form of racemic nucleosides, enzymatic and chemical resolution methods are needed. If successful, such methods would suffer from a practical disadvantage of wasting half of the prepared material.

As demonstrated in the above examples, the art lacks an efficient method to generate β-nucleosides. In particular, with sugar precursors carrying a protected hydroxymethyl group at C-4', low selectivity is encountered during synthesis of β-isomers or racemization problems occur. Specifically, the art lacks a method of producing stereoselectively dioxolanes from sugar intermediates carrying a C-2 protected hydroxymethyl moiety without racemization. Therefore, a general stereoselective synthesis of biologically active β-nucleoside analogues is an important goal.

International patent application publication no. WO92/20669 discloses a method of producing dioxolanes stereoselectively by coupling sugar intermediates carrying C-2 ester moieties with silylated nucleobases and subsequently reducing the C-2 ester group to the desired hydro methyl group. However, over reduction problems in the pyrimidine base have been disclosed (Tse et al. *Tetrahedron Lett.* 1995, 36, 7807–7810).

Nucleoside analogues containing 1,3-dioxolanyl sugars as mimetics of 2',3'-dideoxyfuranosyl rings have been prepared by glycosylating silylated purine and pyrimidine bases with 1,3-dioxolanes containing a C-2 hydroxymethyl and C-4 acetoxy substituents. The crucial coupling reaction is mediated by trimethylsilyltriflate (TMSOT$_f$) or iodotrimethylsilane (TMSI) and produces a mixture of β and α-anomers in 1:1 ratio (Kim et al. *J. Med. Chem.* 1992, 35, 1987–1995 and *J. Med. Chem.* 1993, 36, 30–37; Belleau et al. *Tetrahedron Lett.* 1992, 33, 6948–6952; and Evans et al. *Tetrahedron Asyimetzy* 1992, 4, 2319–2322). By using metal salts as catalysts the β-nucleoside is favoured (Choi et al. *J. Am. Chem. Soc.* 1991, 113, 9377–9379) but racemization or loss of selectivity become a serious limitation (Jin et al. *Tetrahedron Asymetry* 1993, 4, 2111–2114).

SUMMARY OF THE INVENTION

According to an aspect of the present invention, there is provided a process for producing a β-nucleoside analogue compound of formula (III):

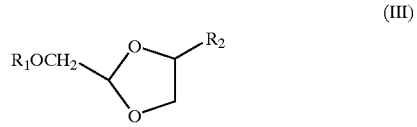

and salts thereof, wherein $R_1$ is a hydroxyl protecting group; and $R_2$ is a purine or pyrimidine base or an analogue thereof, the process comprising glycosylating said purine or pyrimidine base at a temperature below about –10° C., with an intermediate of formula (II):

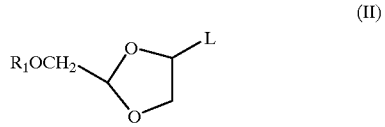

wherein L is halogen.

Subsequent to glycosylation, the compound of formula (III) may then undergo deprotection of the hydroxyl protecting group $R_1$ to give a 1,3-dioxolane nucleoside analogue of formula (I)

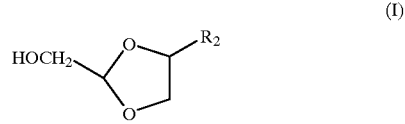

wherein $R_2$ is as previously defined.

DETAILED DESCRIPTION OF THE INVENTION

The present invention provides a novel method for producing dioxolane nucleoside analogues by coupling sugar precursors carrying a C-2 protected hydroxymethyl group with purine or pyrimidine nucleobases in high yield and selectivity in favour of the desired β-isomers.

A <<nucleoside>> is defined as any compound which consists of a purine or pyrimidine base or analogue or derivative thereof, linked to a pentose sugar.

A <<nucleoside analogue or derivative>> as used hereinafter is a compound containing a 1,3-dioxolane linked to a purine or pyrimidine base or analog thereof which may be modified in any of the following or combinations of the following ways: base modifications, such as addition of a substituent (e.g. 5-fluorocytosine) or replacement of one group by an isosteric group (e.g. 7-deazaadenine); sugar modifications, such as substitution of hydroxyl groups by any substituent or alteration of the site of attachment of the sugar to the base (e.g. pyrimidine bases usually attached to the sugar at the N-1 site may be, for example, attached at the N-3 or C-6 site and purines usually attached at the N-9 site may be, for example, attached at N-7.

A purine or pyrimidine base means a purine or pyrimidine base found in naturally occurring nucleosides. An analogue thereof is a base which mimics such naturally occurring bases in that its structure (the kinds of atoms and their arrangement) is similar to the naturally occurring bases but may either possess additional or lack certain of the functional properties of the naturally occurring bases. Such analogues include those derived by replacement of a CH moiety by a nitrogen atom, (e.g. 5-azapyrimidines, such as 5-azacytosine) or conversely (e.g., 7-deazapurines, such as 7-deazaadenine or 7-deazaguanine) or both (e.g., 7-deaza, 8-azapurines). By derivatives of such bases or analogues are meant those bases wherein ring substituent are either incorporated, removed, or modified by conventional substituents known in the art, e.g. halogen, hydroxyl, amino, $C_{1-6}$ alkyl. Such purine or pyrimidine bases, analogs and derivatives are well known to those of skill in the art.

$R_1$ is a hydroxyl protecting group. Suitable protecting groups include those described in detail in *Protective Groups in Organic Synthesis*, Green, John, J. Wiley and Sons, New York (1981). Preferred hydroxyl protecting groups include ester forming groups such as $C_{1-6}$ acyl i.e. formyl, acetyl, substituted acetyl, propionyl, butanoyl, pivalamido, 2-chloroacetyl; aryl substituted $C_{1-6}$ acyl i.e. benzoyl, substituted benzoyl; $C_{1-6}$ alkoxycarbonyl i.e. methoxycarbonyl; aryloxycarbonyl i.e. phenoxycarbonyl. Other preferred hydroxyl protecting groups include ether forming groups such as $C_{1-4}$ alkyl i. e. methyl, t-butyl; aryl $C_{1-6}$ alkyl i.e. benzyl, diphenylmethyl any of which is optionally substituted i.e. with halogen. Particularly preferred hydroxyl protecting groups are t-butoxycarbonyl, benzoyl and benzyl each optionally substituted with halogen. In a more particularly preferred embodiment the $R_1$ hydroxyl protecting group is benzyl.

In a preferred embodiment, $R_2$ is selected from the group consisting of

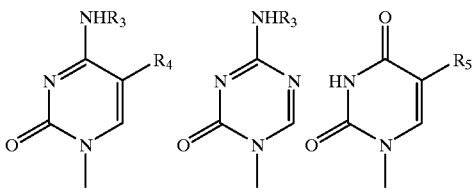

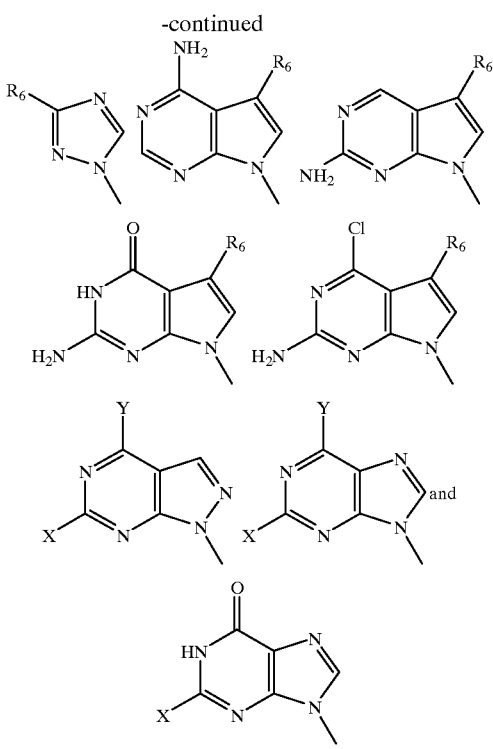

wherein

R$_3$ is selected from the group consisting of hydrogen, C$_{1-6}$ alkyl and C$_{1-6}$ acyl groups;

R$_4$ and R$_5$ are independently selected from the group consisting of hydrogen, C$_{1-6}$ alkyl, bromine, chlorine, fluorine, and iodine;

R$_6$ is selected from the group of hydrogen, halogen, cyano, carboxy, C$_{1-6}$ alkyl, C$_{1-6}$ alkoxycarbonyl, C$_{1-6}$ acyl, C$_{1-6}$ acyloxy, carbamoyl, and thiocarbamoyl; and X and Y are independently selected from the group of hydrogen, bromine, chlorine, fluorine, iodine, amino, and hydroxyl groups.

In a particularly preferred embodiment R$_2$ is

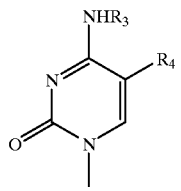

wherein R$_3$ and R$_4$ are as previously defined.

In a particularly preferred embodiment R$_2$ is cytosine or an analogue or derivative thereof. Most preferably R$_2$ is cytosine, N-acetylcytosine or N-acetyl-5-fluorocytosine.

In preferred embodiments R$_3$ is H. In another preferred embodiment R$_3$ is C$_{1-4}$ acyl such as acetyl.

In preferred embodiments R$_4$ and R$_5$ are independently selected from hydrogen, C$_{1-4}$ alkyl such as methyl or ethyl and halogen such as F, Cl, I or Br. In particularly preferred embodiments R$_4$ and R$_5$ are hydrogen. In another particularly preferred embodiment R$_4$ and R$_5$ are F.

In preferred embodiments R$_6$ is selected from hydrogen, halogen, carboxy and C$_{1-4}$ alkyl. in particularly preferred embodiments R$_6$ is H, F or Cl and most preferably H.

In preferred embodiments X and Y are independently selected from the group of H, F or Cl. In a particularly preferred embodiment X and Y are hydrogen.

L is selected from the group consisting of fluoro, bromo, chloro and iodo.

In a particularly preferred embodiment L is an iodo group. In this instance, leaving group (L) may be prepared by displacement of another leaving group (L') i.e. acetoxy with Lewis acids containing an iodo moiety. Preferably such Lewis acids have the formula (IV):

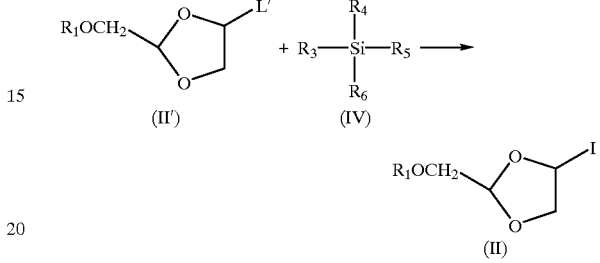

wherein R$_3$, R$_4$ and R$_5$ are independently selected from the group consisting of hydrogen; C$_{1-20}$ alkyl (e.g. methyl, ethyl, ethyl, t-butyl), optionally substituted by halogens (F, Cl, Br, I), C$_{6-20}$ alkoxy (e.g., methoxy) or C$_{6-20}$ aryloxy (e.g., phenoxy); C$_{7-20}$ aralkyl (e.g., benzyl), optionally substituted by halogen, C$_{1-20}$ alkyl or C$_{1-20}$ alkoxy (e.g., p-methoxybenzyl); C$_{6-20}$ aryl (e.g., phenyl), optionally substituted by halogens, C$_{1-20}$ alkyl or C$_{1-20}$ alkoxy; trialkylsilyl; fluoro; bromo; chloro and iodo; and R$_6$ is selected from the group consisting of halogen (F, Cl, Br, I) preferably I (iodo);

L' is a leaving group capable of being displaced by an iodo leaving group using a Lewis acid of formula (IV). Suitable leaving groups L' include acyloxy; alkoxy; alkoxycarbonyl; amido; azido; isocyanato; substituted or unsubstituted, saturated or unsaturated thiolates; substituted or unsubstituted, saturated or unsaturated seleno, seleninyl or selenonyl compounds; —OR wherein R is a substituted or unsubstituted, saturated or unsaturated alkyl group; a substituted or unsubstituted, aliphatic or aromatic acyl group; a substituted or unsubstituted, saturated or unsaturated alkoxy or aryloxy carbonyl group, substituted or unsubstituted sulphonyl imidazolide; substituted or unsubstituted, aliphatic or aromatic amino carbonyl group; substituted or unsubstituted alkyl imidiate group; substituted or unsubstituted, saturated or unsaturated phosphonate; and substituted or unsubstituted, aliphatic or aromatic sulphinyl or sulphonyl group. In a preferred embodiment L' is acetoxy.

In a preferred embodiment, the present invention provides a stereoselective process for producing β-nucleoside analogues of formula (III), and salt or ester thereof, by glycosylation of the purine or pyrimidine base or analogue or derivative thereof, with an intermediate of formula (II) as defined previously under low temperature conditions. Preferably, the glycosylation reaction takes place at temperatures below −10° C. i.e. about −10 to −100° C. and more preferably below −20° C. In a most preferred embodiment the glycosylation reaction occurs between about −20 to −78° C.

The intermediate of formula II is reacted with a silylated purine or pyrimidine base, conveniently in a suitable organic solvent such as a hydrocarbon, for example, toluene, a halogenated hydrocarbon such as dichloromethane (DCM), a nitrile, such as acetonitrile, an amide such as dimethylformamide, an ester, such as ethyl acetate, an ether such as tetrahydrofuran, or a mixture thereof, at low temperatures, such as −40° C. to −78° C. Silylated purine or pyrimidine bases or analogues and derivatives thereof may be prepared as described in WO92/20669, the teaching of which is incorporated herein by reference. Such silylating agents are 1,1,1,3,3,3-hexamethyldisilazane, trimethylsilyl triflate, t-butyldimethylsilyl triflate or trimethylsilyl chloride, with acid or base catalyst, as appropriate. The preferred silylating agent is 1,1,1,3,3,3,-hexamethyldisilazane.

To form the compound of formula (I), appropriate deprotecting conditions include methanolic or ethanolic ammonia or a base such as potassium carbonate in an appropriate solvent such as methanol or tetrahydrofuran for N-4 deacetytion.

Transfer deacetylation hydrogenolysis with a hydrogen donor such as cyclohexene or ammonium formate in the presence of a catalyst such as palladium oxide over charcoal are appropriate for the removal of the 5'-aryl group.

It will be appreciated that the intermediate of formula (II) is constituted by intermediates IIa and IIb:

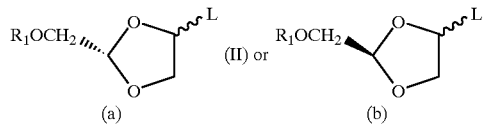

It will be further appreciated that, if the glycosylation step is carried out using equimolar amounts of intermediates IIa and IIb, a racemic mixture of β-nucleosides of formula I is obtained.

It will be apparent to those of skill in the art that separation of the resulting diastereomic mixture, for example after the coupling reaction between compounds of formula II and a silylated base, can be achieved by chromatography on silica gel or crystallization in an appropriate solvent (see, for example: J. Jacques et al. *Enantiomers, Racemates and Resolutions*, pp 251–369, John Wiley and Sons, New York 1981).

However, it is preferred that glycosylation is effected using an optically pure compound of either formula IIa or IIb, thereby producing the desired nucleoside analog in high optical purity.

The compounds of formula IIa or IIb exist as mixture of two diastereomers epimeric at the C-4 centre. We have now found that a single diastereomer, as well as any mixture of the diastereomers comprising the compounds of formula IIa, react with silylated bases to produce β-L nucleosides in high optical purity. The base at C-4 having the cis-stereochemistry relative to the hydroxymethyl moiety at C-2. The rate of the reaction of the two diastereomers of formula IIa with silylated bases may however, be different. Similar findings exist for the intermediates of formula IIb for the synthesis of β-D nucleosides.

In a preferred embodiment, the present invention provides a step for producing anomeric iodides of formula II by reacting known anomeric 2S-benzyloxymethyl-1,3-dioxolane-4S and -4R acetoxy derivatives of formula (V) with iodotrimethylsilane or diiodosilane at low temperatures (−78° C.) prior to glycosylation with silylated pyrimidine or purine base or analogue or derivative thereof (Scheme 1).

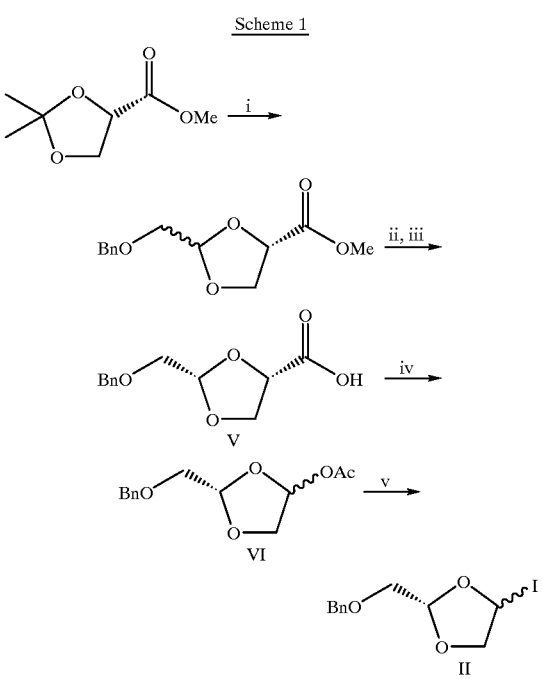

Reagents and conditions:

i)

BnO⏤⏤CHO
/Toluene TSHO/80%/2.7:1.0 cis/trans;

ii) MeOH/LiOH;

iii) Column separation;

iv) Pb(OAc)$_4$/MeCN/Py/2h/RT/80%; and v) TMSI or SiH$_2$I$_2$/CH$_2$Cl$_2$/−78° C.

Suitable methods for producing the anomeric acetoxy intermediate (VI) will be readily apparent to those skilled in the art and include oxidative degradation of benzyloxymethylacetals derived from L-ascorbic acid (Belleau et al. *Tetrahedron Lett.* 1992, 33, 6949–6952) or D-mannitol (Evans et al. *Tetrahedron Asymmetry* 1993, 4, 2319–2322).

We have also found that the known 2S-benzyloxymethyl-1,3-dioxolane-4S-carboxyclic acid (V) can be generated in preference to its 2S,4R isomer by reacting commercially available 2,2-dimethyl-1,3-dioxolane-4S-carboxylic acid with a protected derivative of hydroxyacetaldehyde, such as benzyloxyacetaldehyde, under acidic conditions In the diastereoselective process of this invention, there is also provided the following intermediates:

2S-Benzyloxymethyl-4R-iodo-1,3 dioxolane and 2S-Benzyloxymethyl-4S-iodo-1,3 dioxolane;

β-L-5'-Benzyl-2'-deoxy-3'-oxa-N-4-acetyl-cytidine;

β-L-5'-Benzyloxy-2'-deoxy-3'-oxacytidine;

β-L-5'-Benzyl-2'-deoxy-3'-oxa-5-fluoro-N4-acetyl-cytidine; and

β-L-5'-Benzyl-2'-deoxy-3'-oxa-5-fluorocytidine.

EXAMPLE 1a

2S-Benzyloxymethyl-4R-iodo-1,3 dioxolane and
2S-Benzyloxymethyl-4S-iodo-1,3 dioxolane
(Compound #1)

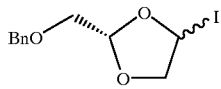

A mixture consisting of 2S-benzyloxymethyl-4S acetoxy-1,3 dioxolane and 2S-benzyloxymethyl-4R-acetoxy-1,3 dioxolane in 1:2 ratio (6g; 23.8 mmol) was dried by azeotropic distillation with toluene in vacuo. After removal of toluene, the residual oil was dissolved in dry dichloromethane (60 ml) and iodotrimethylsilane (3.55 ml; 1.05 eq) was added at −786° C., under vigorous stirring. The dry-ice/acetone bath was removed after addition and the mixture was allowed to warm up to room temperature (15 min.). The $^1$H NMR indicated the formation of 2S-benzyloxymethyl-4R-iodo-1,3-dioxolane and 2S-benzyloxymethyl-4S-iodo-1,3 dioxolane.

$^1$H NMR (300 MHz, CDCl$_3$) δ 3.65–4.25 (2H,m); 4.50–4.75 (4H,m) 5.40–5.55 (1H, overlapping triplets); 6.60–6.85 (1H, d of d); 7.20–7.32 (5H,m).

EXAMPLE 1b

2S-Benzyloxymethyl-4R-iodo-1,3 dioxolane and
2S-Benzyloxymethyl-4S-iodo-1,3 dioxolane
(Compound #1)

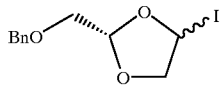

A mixture consisting of 2S-benzyloxymethyl-4S acetoxy-1,3 dioxolane and 2S-benzyloxymethyl-4R-acetoxy-1,3 dioxolane in 1:2 ratio (6g; 23.8 mmol) was dried by azeotropic distillation with toluene in vacuo. After removal of toluene, the residual oil was dissolved in dry dichloromethane (60 ml) and diiodosilane (2.4 ml; 1.05 eq) was added at −78° C., under vigorous stirring. The dry-ice/acetone bath was removed after addition and the mixture was allowed to warm up to room temperature (15 min.). The $^1$H NMR indicated the formation of 2S-benzyloxymethyl-4R-iodo-1,3-dioxolane and 2S-benzyloxymethyl-4S-iodo-1,3 dioxolane. $^1$H NMR (300 MHz, CDCl$_3$) δ 3.65–4.25 (2H,m); 4.50–4.75 (4H,m) 5.40–5.55 (1H, overlapping triplets); 6.60–6.85 (1H, d of d); 7.20–7.32 (5H,m).

EXAMPLE 2

β-L-5'-Benzyl-2'-deoxy-3'-oxa-N-4-acetyl-cytidine
(Compound #2)

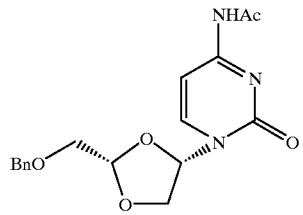

The previously prepared iodo intermediate (example 1) in dichloromethane, was cooled down to −78° C. Persylilated N-acetyl cytosine (1.1 eq) formed by reflux in 1,1,1,3,3,3-hexamethyl disilazane (HMDS) and ammonium sulphate followed by evaporation of HMDS was dissolved in 30 ml of dichloromethane and was added to the iodo intermediate. The reaction mixture was maintained at −78° C. for 1.5 hours then poured onto aqueous sodium bicarbonate and extracted with dichloromethane (2×25 ml). The organic phase was dried over sodium sulphate, the solid was removed by filtration and the solvent was evaporated in vacuo to produce 8.1 g of a crude mixture. Based on $^1$H NMR analysis, the β-L-5'-benzyl-2'-deoxy-3'-oxacytidine and its α-L isomer were formed in a ratio of 5:1 respectively. This crude mixture was separated by chromatography on silica-gel (5% MeOH in EtOAc) to generate the pure β-L (cis) isomer (4.48 g). Alternatively, recrystallization of the mixture from ethanol produces 4.92 g of pure β isomer and 3.18 g of a mixture of β and α-isomers in a ratio of 1:1.

$^1$H NMR (300 MHz, CDCl$_3$) δ 2.20 (3H,S,Ac); 3.87 (2H,m,H-5'), 4.25 (2H,m,H-2'); 4.65 (2H,dd,OCH$_2$Ph); 5.18 (1H,t,H-4'); 6.23 (1H,m,H-1'); 7.12 (1H,d,H-5); 7.30–7.50 (5H,m,Ph); 8.45 (2H,m,NH+H-6).

EXAMPLE 3

β-L-5'-Benzyloxy-2'-deoxy-3'-oxacytidine
(Compound #3)

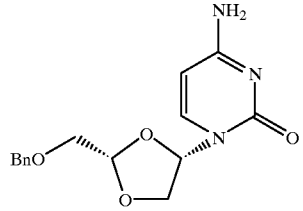

The protected β-L isomer (4.4 g) of example 2 was suspended in saturated methanolic ammonia (250 ml) and stirred at room temperature for 18 hours in a closed-vessel. The solvents were then removed in vacuo to afford the deacetylated nucleoside in pure form.

$^1$H NMR (300 MHz, CDCl$_3$) δ 3.85 (2H,m,H-5'); 4.20 (2H,m,H-2'); 4.65 (2H,dd,OCH$_2$Ph); 5.18 (1H,t,H-4'); 5.43 (1H,d,H-5); 5.50–5.90 (2H,br.S,NH$_2$); 6.28 (1H,m,H-1'); 7.35–7.45 (5H,m,Ph); 7.95 (1H,d,H-6).

EXAMPLE 4

β-L-2'-deoxy-3'-oxacytidine (Compound #4)

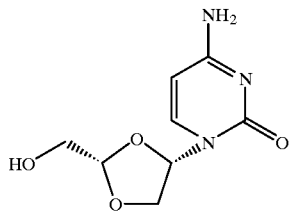

β-L-5'-Benzyl-2'-deoxy-3'-oxacytidine from the previous example, was dissolved in EtOH (200 ml) followed by addition of cyclohexene (6 ml) and palladium oxide (0.8 g). The reaction mixture was refluxed for 7 hours then it was cooled and filtered to remove solids. The solvents were removed from the filtrate by vacuum distillation. The crude product was purified by flash chromatography on silica-gel (5% MeOH in EtOAc) to yield a white solid (2.33 g; 86% overall yield, $\alpha_D^{22}$=−46.7° (c=0.285; MeOH) m.p.= 192–194° C. $^1$H NMR (300 MHz,DMSO-$d_6$) δ 3.63 (2H, dd,H-5'); 4.06 (2H,m,H-2'); 4.92 (1H,t,H-4'); 5.14 (1H,t, OH); 5.70 (1H,d,H-5); 6.16 (2H,dd,H-1'); 7.11–7.20 (2H, brS,NH$_2$); 7.80 (,d,H-6) $^{13}$C NMR (75 MHz,DMSO-$d_6$) δ 59.5 (C-2'); 70.72 (C-5'); 81.34 (C-4'); 93.49 (C-1'); 104.49 (C-5); 140.35 (C-4); 156.12 (C-6); 165.43 (C-2).

EXAMPLE 5

β-L-5'-Benzyl-2'-deoxy-3'-oxa-5-fluoro-N4-acetyl-cytidine (Compound #5)

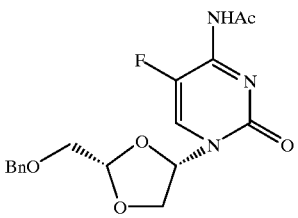

The previously prepared iodo derivatives (example 1) in dichloromethane, was cooled down to −78° C. Persylilated N-acetyl-5-fluorocytosine (1.05 eg) formed by reflux in 1,1,1,3,3,3-hexamethyldisilazane (HMDS) and ammonium sulphate followed by evaporation of HMDS was dissolved in 20 ml of dichloromethane (DCM) and was added to the iodo intermediate. The reaction mixture was maintained at −78° C. for 1.5 hours then poured onto aqueous sodium bicarbonate and extracted with dichloromethane (2×25 ml). The organic phase was dried over sodium sulphate, the solid was removed by filtration and the solvent was evaporated in vacuo to produce 8.1 g of a crude mixture. Based on $^1$H NMR analysis, the β-L-5'-benzyl-2'-deoxy-3'-oxa-5-fluoro-N4-acetyl-cytidine and its α-L isomer were formed in a ratio of 5:1 respectively. This crude mixture was separated by chromatography on silica-gel (5% MeOH in EtOAc) to generate the pure β-L (cis) isomer (4.48 g). Alternatively, recrystallization of the mixture from ethanol produces 4.92 g of pure β isomer and 3.18 g of a mixture of β and α-isomers in a ratio of 1:1.

$^1$H NMR (300 MHz, CDCl$_3$) δ 2.20 (3H,S,Ac); 3.87 (2H,m,H-5'), 4.25 (2H,m,H-2'); 4.65 (2H,dd,OCH$_2$Ph); 5.18 (1H,t,H-4'); 6.23 (1H,m,H-1'); 7.12 (1H,d,H-5); 7.30–7.50 (5H,m,Ph); 8.45 (2H,m,NH+H-6).

EXAMPLE 6

β-l-5'-Benzyl-2'-deoxy-3'-oxa-5-fluorocytidine (Compound #6):

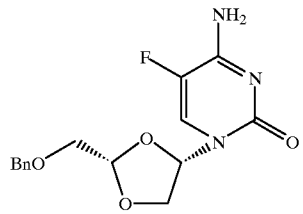

The crude mixture from previous step (example 5) was suspended in methanolic ammonia (100 ml) and stirred for 18 hours at room temperature in a closed reaction vessel. The solvents were removed in vacuo to afford the deacetylated mixture which was separated by flash chromatography on silica gel (2% to 3% MeOH in EtOAc) to yield 1.21 g pure β isomer (yield 45% with respect to this isomer).

EXAMPLE 7

β-L-2'-deoxy-3'-oxa-5-fluorocytidine (Compound #7)

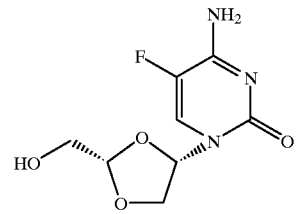

The deacetylated pure β-L isomer (900 mg; 2.8 mmol) prepared as described in example 6 was dissolved in EtOH (40 ml) followed by addition of cyclohexene (3 ml) and palladium oxide catalyst (180 mg). The reaction was refluxed for 24 hours and the catalyst was removed by filtration. The solvents were removed from the filtrate by vacuum distillation. The crude product was purified by flash chromatography on silica-gel (5% to 7% MeOH in EtOAc) to yield a white solid (530 mg ; 82% yield). $(\alpha^{22}_D)$=−44.18° (c=0.98; MeOH).

$^1$H NMR (300 MHz, DMSO-$d_6$); δ 3.62–3.71 (2H,m,H-5); 4.03–4.13 (2H;m,H-2'); 4.91 (1H,t,H-4'); 5.32 (1H,t, OH); 6.11 (1H;t;H-1'); 7.53–7.79 (2H,b,NH$_2$); 8.16 (1H;d, H-6); $^{13}$C NMR (75 MHz, DMSO-$d_6$); δ 59.34 (C-2'); 70.68 (C-5'); 80.78 (C-4'); 104.53-(C-1'); 124.90, 125.22 (C-4); 134.33, 136.73 (C-5); 153.04 (C-2); 156.96, 157.09 (C-6).

EXAMPLE 8

Isomeric Purity Determination of β-L-2'-deoxy-3'-oxacytidine Nucleoside Analogues The determination of the isomeric purity (β-L versus α-L and β-L versus α-D isomers) was determined on a Waters HPLC system consisting of a 600 controller pump for solvent delivery, 486 uv detector, 412 WISP auto sampler and a 740 Waters integrator module. An analytical chiral reverse phase cyclobond I RSP column (Astec, 4.6×250 mm i.d.) was used and packed by the manufacturer with β-cyclodextrin derivatized with R'S-hydroxypropyl ether. The mobile phase consisted of acetonitrile (A) and water containing 0.05% triethylamine (B) with the pH adjusted to 7.05 by glacial acetic acid. The column was operated under isocratic conditions at 0° C. using a mixture of 5% A and 95% B. Such conditions are modifications of those reported in DiMarco et al. (*J. Chromatography*, 1993, –645, 107–114). The flow rate was 0.22 ml/min and the pressure was maintained at 648–660 psi. Detection of nucleosides was monitored by uv absorption at 215 and 265 nm. Samples of β-D isomer and racemic compounds were prepared as reported (Belleau et al. *Tetrahedron Lett* 1992, 33, 6948–6952) and used for internal references and co-injection.

Under these conditions the isomeric purity of compound #4 produced according to example 4 was >99% and that of compound #7 according to example 7, was >96%.

The isomeric purity of dioxolane nucleosides having been prepared according to the general scheme 2, under varying conditions i.e. temperature and Lewis acid is represented in table 1 below. Those prepared at temperatures above –10° C. exhibited reduced stereoselectivity.

Scheme 2

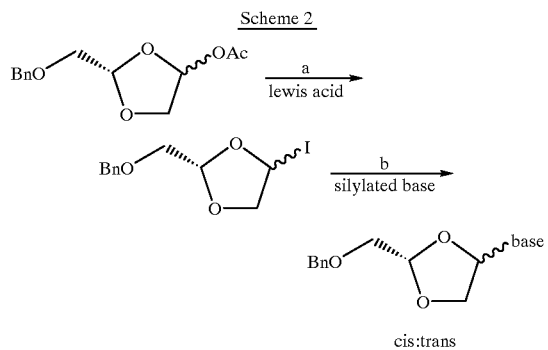

TABLE 1

| Base | Lewis acid | Temperature (° C.) | | Cis:trans |
|---|---|---|---|---|
| 5F-N(Ac)-cytosine | TMSI | a: –78 | b: –78 | 8:1 |
| 5F-N(Ac)-cytosine | SiH$_2$I$_2$ | a: –78 | b: –78 | 7:2 |
| N(Ac)-cytosine | TMSI | a: –78 | b: –78 | 5:1 | note:
all reactions in DCM solvent and bases silylated with HMDS.

We claim:

1. A process, comprising glycosylating a purine or pyrimidine base or an analog thereof in which one or more carbon atoms in the base are substituted by a nitrogen atom, one or more nitrogen atoms in the base are substituted by a carbon atom, or both, or derivative thereof, at a temperature of –10° C. or less, with a compound of formula (IIa) or (IIb):

(IIa)

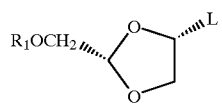

-continued (IIb)

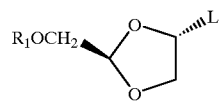

wherein L is a halogen and R$_1$ is a hydroxyl protecting group, to produce a compound of formula (IIIa) or (IIIb):

(IIIa)

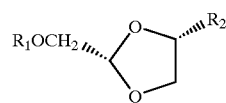

(IIIb)

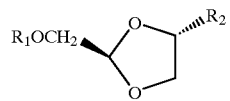

and salts thereof, wherein R$_2$ is a purinyl or pyrmidinyl group or an analog or derivative thereof.

2. The process according to claim 1, wherein L is iodo.

3. The process according to claim 1, wherein R$_1$ is benzyl.

4. The process according to claim 1, wherein said glycosylating step is conducted at a temperature of about –15° C. or less.

5. The process according to claim 1, wherein said glycosylating step is conducted at a temperature of –20° C. or less.

6. The process according to claim 1, wherein said glycosylafing step is conducted at a temperature of –50° C. or less.

7. The process according to claim 1, wherein said glycosylating step is conducted at a temperature of about –78° C.

8. A process, comprising reacting a compound of formula (IIa) or (IIb):

(IIa)

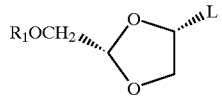

(IIb)

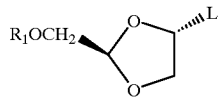

wherein L is a halogen and R$_1$ is a hydroxyl protecting group, with a group R$_2$ at a temperature of about –10° C. or less, wherein R$_2$ is selected from the group consisting of

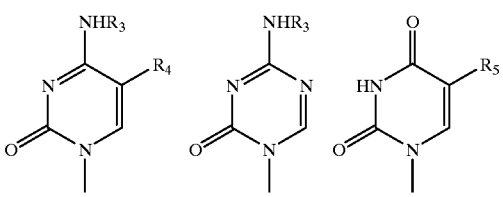

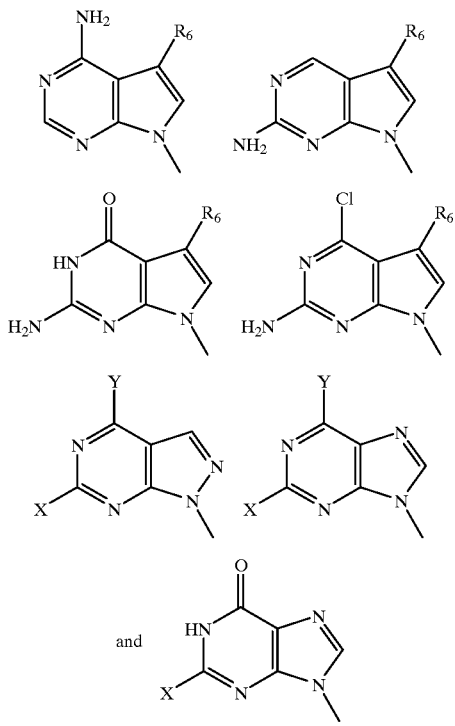

wherein
- R₃ is selected from the group consisting of hydrogen, $C_{1-6}$ alkyl and a group of formula RC(O) wherein R is hydrogen or $C_{1-5}$ alkyl;
- R₄ and R₅ are each independently selected from the group consisting of hydrogen, $C_{1-6}$ alkyl, bromine, chlorine, fluorine and iodine;
- R₆ is selected from the group consisting of hydrogen, halogen, cyano, carboxy, $C_{1-6}$ alkyl, $C_{1-6}$ alkoxycarbonyl, carbamoyl, thiocarbamoyl a group of formula RC(O) wherein R is hydrogen or $C_{1-5}$ alkyl and, a group of formula RC(O)O wherein R is hydrogen or $C_{1-5}$ alkyl; and
- X and Y are each independently selected from the group consisting of hydrogen, bromine, chlorine, fluorine, iodine, amino and hydroxyl, to produce a compound of formula (IIIa) or (IIIb):

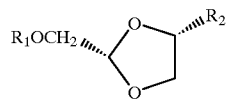

(IIIa)

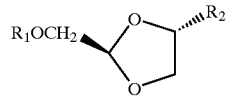

(IIIb)

and salts thereof.

9. The process according to claim 8, wherein R₂ is

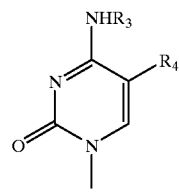

wherein
- R₃ is selected from the group consisting of hydrogen, $C_{1-6}$ alkyl and a group of formula RC(O) wherein R is hydrogen or $C_{1-6}$ alkyl; and
- R₄ is selected from the group consisting of hydrogen, $C_{1-6}$ alkyl, bromine, chlorine, fluorine and iodine.

10. The process according to claim 9, wherein R₃ is hydrogen or acetyl and R₄ is hydrogen or fluorine.

11. The process according to claim 8, wherein said glycosylating step is conducted at a temperature of about −15° C. or less.

12. The process according to claim 8, wherein said glycosylating step is conducted at a temperature of about −20° C. or less.

13. The process according to claim 8, wherein said glycosylating step is conducted at a temperature of about −50° C. or less.

14. The process according to claim 8, wherein said glycosylating step is conducted at a temperature of about −78° C.

* * * * *